United States Patent
Hollard et al.

(10) Patent No.: US 9,554,583 B2
(45) Date of Patent: Jan. 31, 2017

(54) PROCESS FOR THE PRODUCTION OF FREEZE DRIED MICRO-ORGANISMS AND RELATED COMPOSITIONS

(71) Applicant: DuPont Nutrition Biosciences ApS, Copenhagen (DK)

(72) Inventors: Christophe Hollard, McFarland, WI (US); Ronald Agee, Stoughton, WI (US)

(73) Assignee: DUPONT NUTRITION BIOSCIENCES APS (DK)

(*) Notice: Subject to any disclaimer, the term of this patent is extended or adjusted under 35 U.S.C. 154(b) by 0 days.

(21) Appl. No.: 14/362,723

(22) PCT Filed: Dec. 7, 2012

(86) PCT No.: PCT/EP2012/074759
§ 371 (c)(1),
(2) Date: Jun. 4, 2014

(87) PCT Pub. No.: WO2013/083762
PCT Pub. Date: Jun. 13, 2013

(65) Prior Publication Data
US 2014/0335227 A1    Nov. 13, 2014

Related U.S. Application Data

(60) Provisional application No. 61/568,237, filed on Dec. 8, 2011.

(30) Foreign Application Priority Data

Dec. 21, 2011  (GB) .................................. 1121992.0

(51) Int. Cl.
| | | |
|---|---|---|
| A23K 1/10 | (2006.01) | |
| C12N 1/20 | (2006.01) | |
| C12N 1/04 | (2006.01) | |
| A23L 1/30 | (2006.01) | |
| A23L 3/34 | (2006.01) | |
| A23K 1/00 | (2006.01) | |
| A23L 3/44 | (2006.01) | |
| F26B 5/06 | (2006.01) | |
| A23L 3/015 | (2006.01) | |

(52) U.S. Cl.
CPC ............... *A23K 1/009* (2013.01); *A23K 10/18* (2016.05); *A23L 3/015* (2013.01); *A23L 3/44* (2013.01); *A23L 29/065* (2016.08); *A23L 33/135* (2016.08); *C12N 1/04* (2013.01); *C12N 1/20* (2013.01); *F26B 5/06* (2013.01); *A23V 2002/00* (2013.01); *A23Y 2220/03* (2013.01); *A23Y 2240/75* (2013.01)

(58) Field of Classification Search
CPC ......... A23K 1/009; A23L 1/3014; A23L 3/44; C12N 1/04; C12N 1/20
USPC ................................. 426/61; 435/253.4, 252.9
See application file for complete search history.

(56) References Cited

U.S. PATENT DOCUMENTS

| | | | | |
|---|---|---|---|---|
| 4,205,132 A | * | 5/1980 | Sandine | ........... C12N 1/04 426/36 |
| 6,322,994 B1 | * | 11/2001 | Reid | ............................. 435/29 |
| 6,971,187 B1 | | 12/2005 | Pikal et al. | |

FOREIGN PATENT DOCUMENTS

| | | |
|---|---|---|
| WO | 03/018778 A2 | 3/2003 |
| WO | 2011094469 A2 | 8/2011 |
| WO | 2012021783 A2 | 2/2012 |

OTHER PUBLICATIONS

Perry, S. F. 1995. Freeze-Drying and Cryopreservation of Bacteria. Methods in Molecular Biology. 38: 21-30.*
King, V.A., et al., "Controlled low-temperature vacuum dehydration—a new approach for low-temperature and low-pressure food drying". Journal of Food Sci. 54 (1989) pp. 1573-1579.
Knorr, D., "Technology aspects related to microorganisms in functional foods". Trends Food Sci. Technol. 9 (1988) pp. 295-306.
Regier, M., et al., "Microwave- and Microwave Vacuum-drying of Food", Chem. Ing.Tech. 76 (2004) pp. 424-431.
Valdramidis, V.P., et al., "Quantitative description of Listeria monocytogenes inactivation kinetics with temperature and water activity as the influencing factors; model prediction and methodological validation on dynamic data", J. Food Eng. 76 (2005) p. 79-88.
Bauer et al., "Combined influence of fermentation and drying conditions on survival and metabolic activity of starter and probiotic cultures after low-temperature vacuum drying", Journal of Biotechnology (2011), doi: 10.1016/jbiotec.2011.06.010.
Chen, et al., "The Effects of Freeze Drying and Rehydration on Survival of Microorganisms in Kefir", Asian-Aust. J. Anim. Sci. 2006, vol. 19, No. 1:126-130.
King et al., "A response surface methodology approach to the optimization of controlled low-temperature vacuum dehydration", Food Research International 25 (1992) pp. 1-8.
Perry, Stephen F., "Freeze-Drying and Cryopreservation of Bacteria", Molecular Biotechnology, 1998, vol. 9, pp. 59-64.
International Search Report and Written Opinion for PCT/EP2012/074759 mailed Feb. 20, 2013.

(Continued)

*Primary Examiner* — Hamid R Badr

(57) ABSTRACT

The present invention provides a process for the preparation of freeze dried microorganism composition, comprising the step of (i) subjecting a frozen composition comprising micro-organisms to a drying pressure of from 133 Pa [1000 mT] to 338 Pa [2540 mT] such that at the drying pressure the frozen composition is dried by sublimation of water present in the frozen composition to provide a freeze dried composition comprising the micro-organisms.

16 Claims, 2 Drawing Sheets

(56) References Cited

OTHER PUBLICATIONS

Intellectual Property Office, Patents Act 1977: Search Report Under Section 17 for GB Application No. 1121992.0 dated Apr. 20, 2012.
International Search Report and Written Opinion of the International Searching Authority for PCT/EP2012/974759, mailed Feb. 20, 2013; the whole document.
Krishan K. Selwal et al: "Effect of freeze drying process on some properties of *Streptococcus thermophilus* isolated from dairy products", Brazilian Journal of Microbiology, vol. 42, Oct. 1, 2011 (Oct. 1, 2011), pp. 1500-1505, XP55053116, ISSN: 1517-8382 the whole document.
V.A.-E. King et al: "Dehydration of Lactobacillus acidophilus", Process Biochemistry, vol. 28, No. 1, Jan. 1, 1994 (Jan. 1, 1994), pp. 47-52, XP55053084, ISSN: 1359-5113, DOI: 10.1016/0032-9592(94)80035-9 the whole document.
Kurtmann L et al: "Storage stability of freeze-dried Lactobacillus acidophilus (La-5) in relation to water activity and presence of oxygen and ascorbate", Cryobiology, Academic Press Inc, US, vol, 58, No. 2, Apr. 1, 2009 (Apr. 1, 2009), pp. 175-180, XP025988708, ISSN: 0011-2240. DOI: 10.1016/J.CRYOBIOL.2008.12.001 [retrieved on Dec. 11, 2008] the whole document.

\* cited by examiner

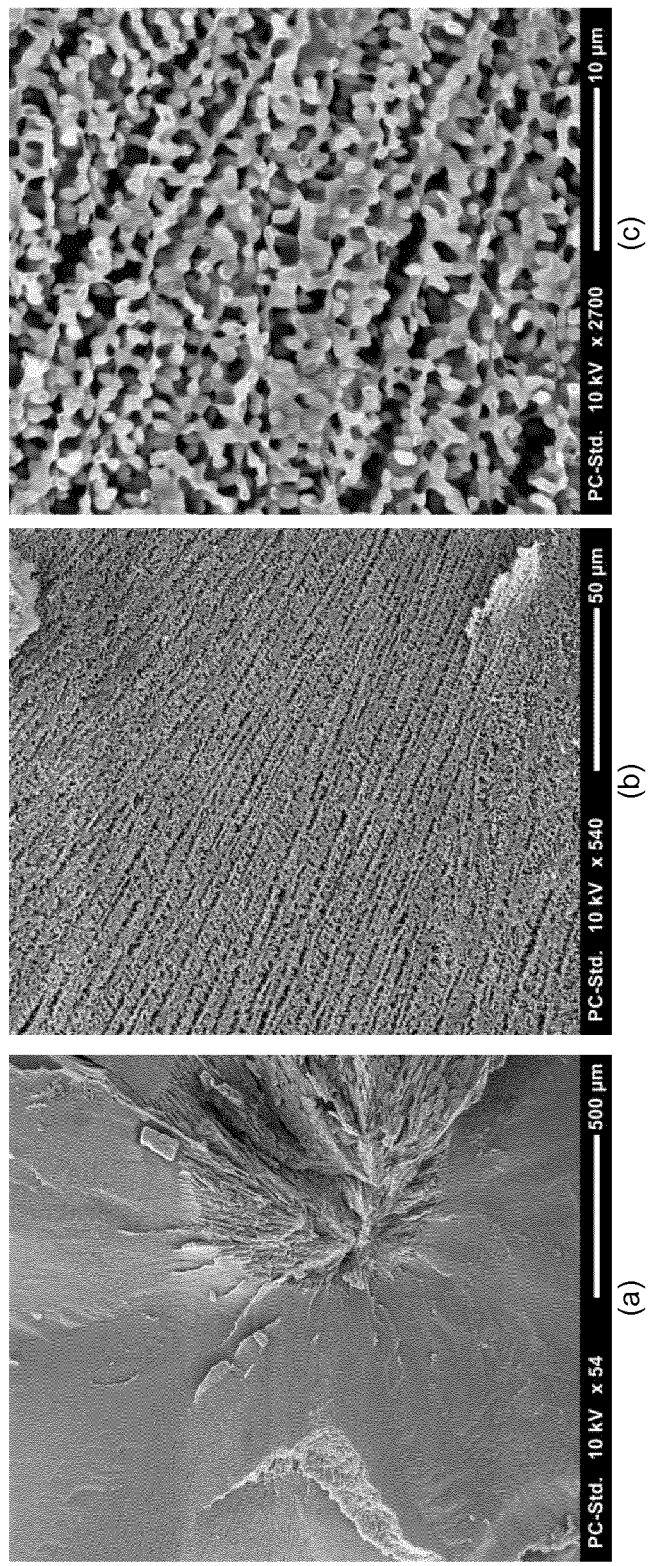
Figure 1. Scanning electron microscope images of the interior of a conventionally freeze-dried pellet of a strain of S. thermophilus. (a) 54X magnification of dried pellet; (b) 540X magnification of dried pellet; (c) 2700X magnification of dried pellet. The images demonstrate a finely textured and homogeneous structure of the cell/protectant matrix.

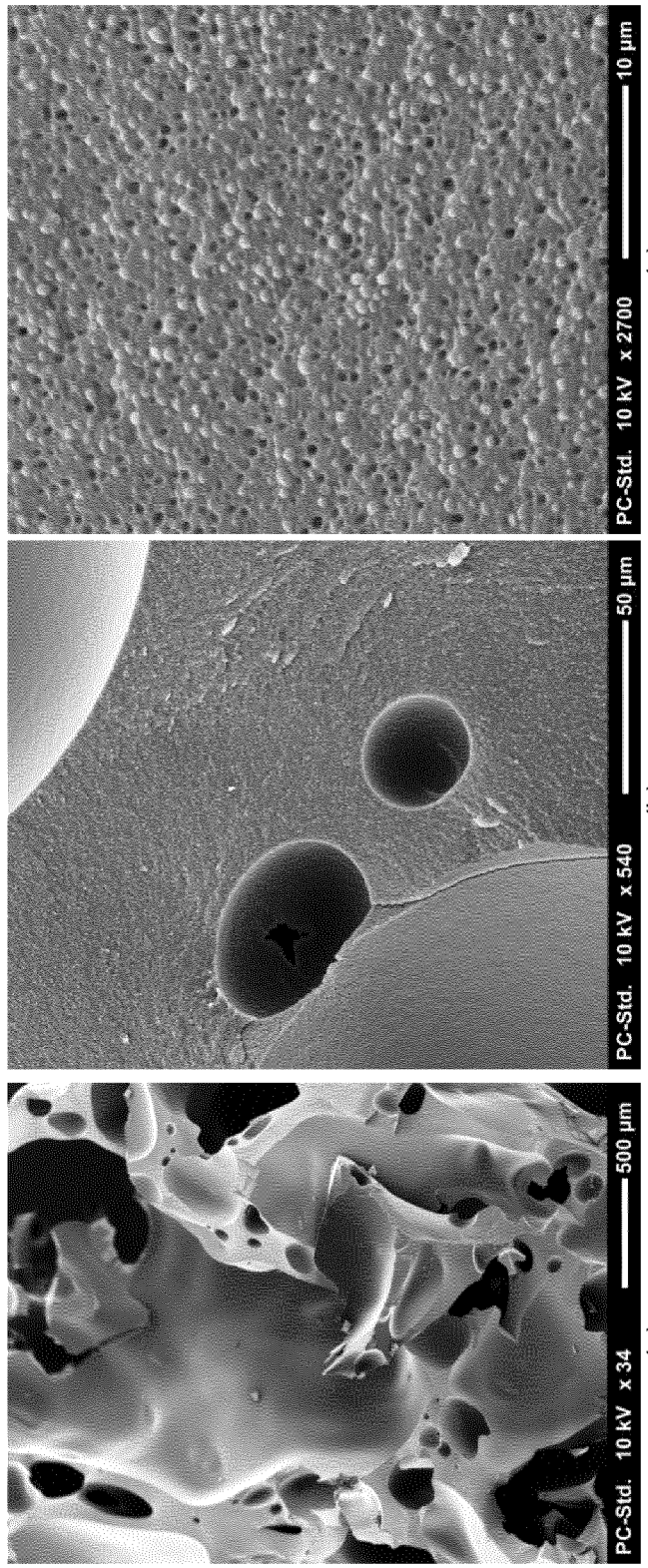

Figure 2. Scanning electron microscope images of the interior of a high-pressure freeze-dried pellet of a strain of S. thermophilus. (a) 34X magnification of dried pellet; (b) 540X magnification of dried pellet; (c) 2700X magnification of dried pellet (what look like holes in this photo are pits where individual cells have been knocked out of place on this fractured surface). The images demonstrate a rearrangement of the structure of the cell/protectant matrix.

PROCESS FOR THE PRODUCTION OF FREEZE DRIED MICRO-ORGANISMS AND RELATED COMPOSITIONS

CLAIM FOR PRIORITY

This application claims priority under 35 USC 371 to International Application No, PCT/EP2012/074759, filed on Dec. 7, 2012, which claims priority to U.S. Provisional Patent Application No. 61/568,237, tiled on Dec. 8, 2011, and British Patent Application No. 1121992.0, which was tiled Dec. 21, 2011, each of which is hereby incorporated by reference in its entirety.

BACKGROUND

As discussed in Bauer et al (Journal of Biotechnology, 2011, in press), in the manufacture of food, there is a demand of stable and well-conditioned starter, protective and probiotic cultures. One of the well established preservation (conservation) processes used during the preparation of these cultures is freeze drying, as it is known to be a gentle drying method leading to minimal damage in micro-organisms. Freeze-drying, also called lyophilisation, is a preservation (or conservation) process whereby the material is frozen (for example into blocks, drops or pellets) at a temperature of below 0° C. The surrounding pressure is then reduced to a range from 10-80 Pa (75-600 mTorr) (Bactéries lactiques De la génétique aux ferments, 2008), generally around 13-27 Pa (100-200 mTorr) and enough heat is added to allow the frozen water in the material to sublime directly from the solid phase to the gas phase. The material can be frozen into the freeze-dryer or introduced directly under a frozen form into the freeze-dryer.

However, freeze drying is a lengthy and energy intensive process (Knorr, 1998; Regier et al., 2004). Moreover, the survival of some bacterial strains is negatively affected by the freezing process (Meryman et al., 1977; Meryman, 2007).

An alternative drying method is vacuum drying, which works at positive temperatures by applying vacuum. Using this drying method at conventional conditions (temperature range between 30 and 80° C.) may cause high losses of cells due to heat damage (Valdramidis et al., 2005). However, heat stresses can be reduced by further reducing the chamber pressure to values just above the triple point of water, which leads to low product temperatures close to 0° C. This process is referred to as Controlled Low-Temperature Vacuum Dehydration (CLTV). King et al. (1989) developed this method for the drying of sensitive food ingredients and also showed that it is applicable to the drying of micro-organisms such as Lactobacillus acidophilus (King and Su, 1993).

Probiotics are well known and are used as dietary supplements. Some probiotics have been preserved by freeze-drying. It is also known that cells which are freeze-dried in the presence of protective agents are better suited to maintain their viability and stability than cells which are freeze-dried without the addition of said protective agents. So generally a protectant is mixed with fresh cell concentrate prior the freeze-drying step.

Freeze-drying can be performed using different techniques. In particular freeze-drying can be performed by tray drying. In this process, the stabilized cell concentrate is loaded directly into freeze dryer trays. The cells are frozen by contact with shelves maintained at a freezing temperature and freeze-dried in a commercial freeze-drier. The resulting cake may then be milled to make a powder, for example which is used in probiotic blends.

Another common freeze-drying process used to preserve cultures is to freeze-dry them in frozen pellet form. The frozen pellets may be formed by dripping stabilized culture onto a chilled surface (such as a chilled barrel or a chilled belt) or into liquid nitrogen. The frozen pellets can be produced and stored independently of freeze-drier availability, and can be easily loaded into freeze drier trays. The resulting dry pellets may then be milled to make a powder, for example which is used in probiotic blends.

Probably the biggest difference between tray-drying and freeze-drying pellets is the rate of freezing. During both freezing processes ice crystals of pure water form, pushing together cells and dissolved solutes into the interstitial spaces between the crystals. When freezing in liquid nitrogen the ice crystals form nearly instantaneously, while freezing in trays allows the ice crystals to grow slowly and hence to a larger size. Freeze-drying removes the ice crystals leaving behind a matrix of interstitial spaces of now dry material. Scanning Electron Microscopy (SEM) of dried material shows that pelletized materials using standard freeze-drying processes have microscopic channels and interstitial matrices and cells are at, or near, the surface. On the contrary tray-dried materials have much larger channels and interstitial matrices and the cells are encapsulated within the matrix material leading to a better protection of the cells. On the other part, standard tray-drying processes are time-consuming in comparison with standard pellets freeze-drying ones, especially due to two factors: a) the slow freezing time limited by heat transfer from the shelves to the material; b) the slow drying time due to the longer distance needed for water to escape from cells (the resulting cake obtained by the tray-drying process are larger in size than the pellets). Another issue linked with tray drying is the difficulty required by its logistics, e.g. the freeze-drier must be close to the fermentation and the timing of the fermentation harvest and drying must be synchronized.

Therefore there is a need to develop an improved freeze-drying process allowing enhanced characteristics of the micro-organisms (such as a better stability).

The present invention alleviates the problems of the prior art.

In one aspect the present invention provides a process for the preparation of freeze dried micro-organism composition, comprising the step of
(i) subjecting a frozen composition comprising micro-organisms to a drying pressure of from 133 Pa [1000 mT] to 338 Pa [2540 mT] such that at the drying pressure the frozen composition is dried by sublimation of water present in the frozen composition to provide a freeze dried composition comprising the micro-organisms.

In one aspect the present invention provides a process for the preparation of a food or feed, the process comprising
  (a) preparing a freeze dried micro-organism by a process comprising the step of
    (i) subjecting a frozen composition comprising micro-organisms to a drying pressure of from 133 Pa [1000 mT] to 338 Pa [2540 mT] such that at the drying pressure the frozen composition is dried by sublimation of water present in the frozen composition to provide a freeze dried composition comprising the micro-organisms;
  (b) combining the freeze dried micro-organism composition with a foodstuff or feedstuff.

In one aspect the present invention provides a freeze dried micro-organism composition obtainable by a process comprising the step of (i) subjecting a frozen composition comprising micro-organisms to a drying pressure of from 133 Pa [1000 mT] to 338 Pa [2540 mT] such that at the drying pressure the frozen composition is dried by sublimation of water present in the frozen composition to provide a freeze dried composition comprising the micro-organisms.

In one aspect the present invention provides a freeze dried micro-organism composition prepared by a process comprising the step of (i) subjecting a frozen composition comprising micro-organisms to a drying pressure of from 133 Pa [1000 mT] to 338 Pa [2540 mT] such that at the drying pressure the frozen composition is dried by sublimation of water present in the frozen composition to provide a freeze dried composition comprising the micro-organisms.

In one aspect the present invention provides a food or feed comprising (a) a freeze dried micro-organism composition as defined herein; and
(b) a foodstuff or feedstuff.

In one aspect the present invention provides use of drying pressure to prepare a freeze dried micro-organism composition having improved stability and/or improved cell count and/or increased density and/or improved dispersibility, wherein a drying pressure of from 133 Pa [1000 mT] to 338 Pa [2540 mT] is applied to a frozen composition comprising micro-organisms to dry the frozen composition by sublimation of water present in the frozen composition.

Aspects of the invention are defined in the appended claims.

The present invention provides novel drying techniques for the preparation of freeze dried compositions containing micro-organisms. In particular the present invention provides a process in which frozen compositions containing micro-organisms are freeze-dried.

In this process freeze-drying is performed at pressures which are higher than those normally used for freeze-drying. The skilled man would not have expected to obtain increased micro-organisms characteristics, such as stability, since it would be expected that a high pressure would have been damaging for the micro-organisms.

An advantage of the present invention is that this process (i.e. the use of a high pressure for freeze-drying micro-organisms) may be implemented in different drying techniques such as pellet drying and tray-drying, leading to improved results.

In comparison with the dried pellets obtained using standard freeze-drying techniques (such process using a pressure of 100 mT), cell counts, shelf stability, density and dispersibility of the freeze-dried micro-organisms are enhanced.

In comparison with standard tray-drying process, it has been found that the cell counts and the cell stability of the compositions freeze-dried in accordance with the present invention surpass the ones obtained for commercially tray-dried material. Furthermore the bulk density of freeze-dried compositions in accordance with the present invention after milling is equivalent to the best tray-dried products. Moreover scanning electron microscopy (SEM) images indicate that cells of micro-organisms in the present compositions are encapsulated in a matrix; it is understood that this translates to their better stability.

For ease of reference, these and further aspects of the present invention are now discussed under appropriate section headings. However, the teachings under each section are not necessarily limited to each particular section.

PREFERRED ASPECTS

Micro-Organism

As discussed herein the frozen composition comprises one or more micro-organisms. In the present invention "micro-organism" or "micro-organisms" are used interchangeably to encompass one or more micro-organisms. Preferably the micro-organisms are selected from the group consisting of yeasts, moulds, fungi, bacteria and mixtures thereof.

In one aspect the micro-organisms are selected from yeasts. Examples of suitable yeasts are: *Kluyveromyces* spp, *Debaryomyces* spp, *Yarrowia* spp, *Pichia* spp, *Williopsis* spp, *Saccharomyces* spp.

In one aspect the micro-organisms are selected from moulds. In one aspect the micro-organisms are selected from fungi. Examples of suitable fungi/moulds are: *Penicillium* spp, *Geotrichum* spp, *Lecanicillium* spp, *Trichothecium* spp.

In one aspect the micro-organisms are selected from one or more strains of bacteria. Examples of suitable bacteria are: coryneform bacteria such as for example *Arthrobacter* spp, *Corynebacterium* spp, *Brevibacterium* spp; lactic acid bacteria; Micrococcaceae and bacteria of the *Staphylococcus* genus.

In one preferred aspect, the one or more strains of bacteria are selected from lactic acid bacteria. According to the invention, the terms "lactic acid bacteria" or "lactic acid bacterium" includes any bacterium capable of producing, as the major metabolic end product of carbohydrate fermentation, lactic acid or at least one of its derivatives (including, but not limited to, propionic acid). The term is therefore intended to include propionic acid bacteria (PAB), which produce propionic acid as a carbohydrate fermentation product.

Preferably the bacteria according to the present invention are lactic acid bacteria which are generally recognized as safe for animal or human consumption (i.e. GRAS approved).

Suitable bacteria may be selected from the genus *Lactococcus, Lactobacillus, Leuconostoc, Bifidobacterium, Carnobacterium, Enterococcus, Propionibacterium, Pediococcus, Streptococcus* and mixtures thereof. Typically, the lactic acid bacteria are selected from the species, subspecies or biovarieties *Leuconostoc* spp., *Lactococcus lactis* subsp. *cremoris, Lactococcus lactis* subsp. *lactis, Lactococcus lactis* subsp. *lactis* biovariety diacetilactis, *Lactobacillus acidophilus, Lactobacillus alimentarius, Lactobacillus casei, Lactobacillus coryneformis, Lactobacillus gasseri, Lactobacillus kefiri, Lactobacillus brevis, Lactobacillus helveticus, Lactobacillus paracasei* ssp, *Lactobacillus rhamnosus, Lactobacillus salivarius, Lactobacillus curvatus, Lactobacillus delbrueckii* subsp. *bulgaricus, Lactobacillus delbrueckii* subsp. *lactis, Lactobacillus delbrueckii* subsp. *delbrueckii, Lactobacillus sakei, Lactobacillus reuteri, Lactobacillus fermentum, Lactobacillus farciminis, Lactobacillus plantarum, Lactobacillus paraplantarum, Lactobacillus crispatus, Lactobacillus gasseri, Lactobacillus johnsonii, Lactobacillus jensenii, Lactobacillus animalis, Lactobacillus pentosus, Lactobacillus franciscensis, Bifidobacterium animalis* subsp. *lactis, Bifidobacterium bifidium, Bifidobacterium longum, Bifidobacterium animalis* subsp. *animalis, Bifidobacterium breve, Bifidobacterium infantis, Bifidobacterium catenulatum, Bifidobacterium pseudo-*

*catenulatum, Bifidobacterium adolescentis, Bifidobacterium angulatum,* and combinations of any thereof.

In a preferred embodiment, the micro-organism is a bacterium, preferably a bacterium selected from the group consisting of bacteria from the *Acetobacter, Bifidobacterium, Carnobacterium, Enterococcus, Lactococcus, Lactobacillus, Leuconostoc, Pediococcus, Oenococcus, Propionibacterium,* and/or *Streptococcus* genus. In a preferred embodiment, said bacterium is a bacterium selected from the group consisting of bacteria from the *Lactococcus, Lactobacillus, Leuconotoc, Bifibobacterium, Pediococcus,* and/or *Streptococcus* genus. In one preferred embodiment the lactic acid bacteria are selected from *Streptococcus thermophilus* and *Lactobacillus acidophilus.*

In one preferred aspect the micro-organisms are selected from probiotics or Direct Fed Microbials (DFM). According to the invention "probiotics" or "DFMs" means live micro-organisms which when administered in adequate amounts confer a health benefit on the host, the host being a human in the case of probiotics and an animal in the case of DFMs. The probiotic micro-organisms or DFMs most commonly used are principally bacteria and yeasts of the following genera: *Lactobacillus* spp., *Streptococcus* spp., *Enterococcus* spp., *Bifidobacterium* spp. and *Saccharomyces* spp.

Freezing

As discussed herein a frozen composition comprising micro-organisms is subject to a drying pressure such that at the drying pressure the frozen composition is dried by sublimation of water present in the frozen composition. It will be appreciated by one skilled in the art that the frozen composition comprising micro-organisms may be prepared by any suitable method. It will be further understood by one skilled in the art that the freezing step to provide the frozen composition is not an essential step of the present invention. In other words, the composition may be already frozen and provided to the present process. In a preferred embodiment the frozen composition comprising micro-organisms is under the form of frozen pellets.

However in another preferred aspect, a step of the process of the present invention is the freezing of a composition comprising micro-organisms to provide the frozen composition. Thus in one preferred aspect the process comprises the additional step of (i') freezing a composition comprising micro-organisms to provide the frozen composition of step (i). It will be appreciated by one skilled in the art that step (i') in which a composition comprising micro-organisms is frozen to provide the frozen composition must be performed prior to step (i) so as to provide the frozen composition to step (i).

Therefore a preferred embodiment of the invention is a process for the preparation of freeze dried micro-organism composition, comprising the steps of (i') freezing a composition comprising micro-organisms to obtain a frozen composition comprising micro-organisms, (i) subjecting said frozen composition comprising micro-organisms to a drying pressure of from 133 Pa [1000 mT] to 338 Pa [2540 mT] such that at the drying pressure the frozen composition is dried by sublimation of water present in the frozen composition to provide a freeze dried composition comprising the micro-organisms.

In a specific embodiment step (i') is performed by spreading out the micro-organism composition into shelves maintained at a freezing temperature (tray-drying process). Preferably step (i') is a step of preparation of frozen pellets, wherein the pellets are formed by dripping micro-organism composition onto a chilled surface (such as a chilled barrel or a chilled belt) or into liquid nitrogen. Preferably step (i') is a step of preparation of frozen pellets by dripping the micro-organism composition into liquid nitrogen (pellet-drying process).

The freezing may be performed by any suitable process. In one aspect a composition comprising the micro-organism is frozen to prepare frozen pellets. Such pellets are typically prepared by dripping a liquid composition containing the micro-organism into liquid nitrogen. Thus in one preferred aspect the present invention includes the step of freezing a liquid composition comprising micro-organisms by dripping the liquid composition into liquid nitrogen to prepare frozen pellets and subsequently utilising the frozen pellets in step (i) of the present process.

The composition containing the micro-organism may be frozen at any suitable temperature so that the micro-organism is then in a form for freeze drying. In one preferred aspect the composition comprising micro-organisms is frozen at a temperature of less than 0° C., preferably from −196° C. to −1° C., preferably from −196° C. to −17° C., preferably from −196° C. to −40° C. In some embodiments the composition comprising micro-organisms is frozen at a temperature of from −40° C. to −10° C., for example when using tray-drying. In one preferred aspect the composition comprising micro-organisms is frozen at a temperature of from −196° C. to −130° C., for example when preparing frozen pellets.

Composition

It will be appreciated by one skilled in the art that the freeze dried micro-organism composition may contain components in addition to the micro-organism. Thus in one aspect the freeze dried micro-organism composition further comprises additional components such as at least a protectant.

The protectant (or protective agent) may be selected from cryoprotectants, lyoprotectants and mixtures thereof.

Cryoprotectants can be defined as substances used to prevent or reduce damage to cells or tissues during freezing and to further prevent or reduce damage during frozen storage. Cryoprotectants often work by changing the characteristics of ice.

Lyoprotectants can be defined as substances used to prevent or reduce damage to cells or tissues during desiccation or freeze drying and optionally to further prevent or reduce damage during dry storage. Lyoprotectants often work by protecting biological structures after water has been removed.

Some substances may act as both cryoprotectants and lyoprotectants.

Various protective agents have thus been used in the art, with varying degrees of success. These protective agents include antioxidants, amino acids, proteins, protein hydrolysates, certain polymers, skim milk, glycerol, carbohydrate such as oligosaccharides and polysaccharides. Suitable examples of proteins or protein hydrolysates include the ones selected from the group consisting of Malt extract, Skimmed milk powder, Whey powder, Yeast extract, Gluten, Collagen, Gelatin, Elastin, Keratin, and Albumins.

The protectant may also preferably be a compound involved in bio-synthesis of nucleic acids.

Preferably, the protectant is a carbohydrate. Preferred suitable carbohydrates include the ones selected from the group consisting of pentoses (e.g. ribose, xylose), hexoses (e.g. fructose, mannose, sorbose), disaccharides (e.g. sucrose, trehalose, melibiose, lactulose), oligosaccharides (e.g. raffinose), oligofructoses (e.g. Actilight, fribroloses), polysaccharides (e.g. maltodextrins, Xanthan Gum, pectin, alginate, Microcrystalline cellulose, Dextran, PEG), and sugar alcohols (sorbitol, manitol, lactitol, maltitol, glycol, glycerol, erythritol, threitol, arabitol, xylitol, ribitol, dulcitol, iditol, isomalt and polyglycitol). In one aspect, the carbohydrate is a carbohydrate with a molecular weight (MW) from 150 to 100000 g/mol, more preferably 250 to 100000 g/mol, even more preferably from 300 to 40000 g/mol and most preferably from 500 to 15000 g/mol. Preferably, the protectant is selected from trehalose sucrose and maltodextrin. In one aspect of the invention the protectant is trehalose.

The protectant may be added to the composition of the present invention in any suitable amount to provide the desired protection against, for example freezing or freeze drying. Typical amounts of protectant are known to one skilled in the art and may be readily identified by one skilled in the art. In one aspect protectant is provided in the present freeze dried micro-organism composition in an amount of less than 90 wt % based on the total weight of the freeze dried micro-organism composition, such as in an amount of less than 85 wt % based on the total weight of the freeze dried micro-organism composition, such as in an amount of less than 80 wt % based on the total weight of the freeze dried micro-organism composition, such as in an amount of less than 75 wt % based on the total weight of the freeze dried micro-organism composition, such as in an amount of less than 70 wt % based on the total weight of the freeze dried micro-organism composition, such as in an amount of less than 65 wt % based on the total weight of the freeze dried micro-organism composition, such as in an amount of from 40 to 80 wt % based on the total weight of the freeze dried micro-organism composition, such as in an amount of from 50 to 70 wt % based on the total weight of the freeze dried micro-organism composition, such as in an amount of at least 10 wt % based on the total weight of the freeze dried micro-organism composition, such as in an amount of at least 20 wt % based on the total weight of the freeze dried micro-organism composition, such as in an amount of at least 30 wt % based on the total weight of the freeze dried micro-organism composition, such as in an amount of at least 40 wt % based on the total weight of the freeze dried micro-organism composition, such as in an amount of at least 50 wt % based on the total weight of the freeze dried micro-organism composition.

The protectant may be added to the micro-organism composition such that it is incorporated in the freeze dried micro-organism composition. In a preferred aspect the protectant is added to the micro-organism composition prior to freezing.

In another embodiment, the process comprises a further step of addition of a protectant before step (i) and/or before the step of freezing (i').

The freeze dried micro-organism composition may contain the micro-organism, such as the one or more strains of bacteria, in a suitable amount dependent on the final use of the composition. In one preferred aspect the freeze dried micro-organism composition comprises the one or more strains of bacteria in an amount of 1E8 to 5E12 CFU/g, preferably 1E9 to 1E12 CFU/g, preferably 1E10 to 1E12 CFU/g, preferably 1E11 to 1E12 CFU/g of freeze dried micro-organism composition In one aspect the protectant that may be used contains phosphate salt at a low level. In one aspect the freeze dried composition contains low amounts of phosphate salts. In one aspect the freeze dried composition contain low amounts of phosphates. By 'low amounts' it is meant that the composition contains less than 15 wt %, preferably less than 12 wt %, preferably less than 10 wt %, preferably less than 8 wt %, preferably less than 5 wt %, preferably less than 3 wt %, preferably less than 2 wt %, preferably less than 1 wt %, preferably less than 0.5 wt % of the material based on the total weight of the composition.

In one aspect the protectant that may be used is not or does not contain a phosphate salt. In one aspect the freeze dried composition is substantially free of phosphate salts. In one aspect the freeze dried composition is substantially free of phosphates. By 'substantially free' it is meant that the composition contains less than 0.1 wt %, preferably less than 0.05 wt %, preferably less than 0.02 wt %, preferably less than 0.01 wt %, preferably less than 0.005 wt %, preferably less than 0.002 wt %, preferably less than 0.001 wt %, preferably less than 0.0001 wt %, preferably less than 0.00001 wt % of the material based on the total weight of the composition.

Freeze Drying

As discussed herein, a frozen composition comprising micro-organisms is subjected to a drying pressure of from 133 Pa [1000 mT] to 338 Pa [2540 mT] such that at the drying pressure the frozen composition is dried by sublimation of water present in the frozen composition, to thereby provide a freeze dried composition comprising the micro-organisms.

Further preferred pressures which may be applied to the frozen composition are
from 133 Pa [1000 mT] to 330 Pa [2480 mT].
from 133 Pa [1000 mT] to 320 Pa [2400 mT].
from 133 Pa [1000 mT] to 310 Pa [2330 mT].
from 133 Pa [1000 mT] to 300 Pa [2250 mT].
from 133 Pa [1000 mT] to 280 Pa [2100 mT].
from 133 Pa [1000 mT] to 275 Pa [2060 mT].
from 133 Pa [1000 mT] to 270 Pa [2030 mT].
from 133 Pa [1000 mT] to 260 Pa [1950 mT].
from 133 Pa [1000 mT] to 250 Pa [1880 mT].
from 133 Pa [1000 mT] to 240 Pa [1800 mT].
from 133 Pa [1000 mT] to 230 Pa [1730 mT].
from 133 Pa [1000 mT] to 220 Pa [1650 mT].
from 133 Pa [1000 mT] to 210 Pa [1580 mT].
from 133 Pa [1000 mT] to 200 Pa [1500 mT].

Further preferred pressures which may be applied to the frozen composition are
from 140 Pa [1050 mT] to 338 Pa [2540 mT].
from 160 Pa [1200 mT] to 338 Pa [2540 mT].
from 180 Pa [1350 mT] to 338 Pa [2540 mT].
from 200 Pa [1500 mT] to 338 Pa [2540 mT].
from 220 Pa [1650 mT] to 338 Pa [2540 mT].
from 240 Pa [1800 mT] to 338 Pa [2540 mT].
from 260 Pa [1950 mT] to 338 Pa [2540 mT].
from 280 Pa [2100 mT] to 338 Pa [2540 mT].
from 300 Pa [2250 mT] to 338 Pa [2540 mT].
from 320 Pa [2400 mT] to 338 Pa [2540 mT].

Further preferred pressures which may be applied to the frozen composition are
from 140 Pa [1050 mT] to 320 Pa [2400 mT].
from 160 Pa [1200 mT] to 300 Pa [2250 mT].
from 160 Pa [1200 mT] to 280 Pa [2100 mT].
from 160 Pa [1200 mT] to 260 Pa [1950 mT].
from 160 Pa [1200 mT] to 240 Pa [1800 mT].
from 160 Pa [1200 mT] to 220 Pa [1650 mT].
from 170 Pa [1280 mT] to 210 Pa [1580 mT].
from 180 Pa [1350 mT] to 200 Pa [1500 mT].

It will be understood by one skilled in the art that drying of frozen compositions in the process known as freeze drying involves applying a reduced pressure to a frozen material and then allowing the increase of the temperature of the frozen material such that water present in the frozen material sublimes. In a preferred aspect of the present invention, once the reduced pressure described herein has been applied in step (i) the composition is subjected to a shelf temperature of from −40° C. to 110° C., preferably −30° C. to 100° C., preferably −20° C. to 90° C., preferably −10° C. to 80° C., preferably 0° C. to 70° C., preferably 0° C. to 60° C., preferably 10° C. to 40° C. preferably 10° C. to 30° C., preferably 15° C. to 30° C., more preferably in step (i) the composition is subjected to a shelf temperature of approximately 25° C.

It will be understood by one skilled in the art that the increased temperature applied to the frozen material such that water present in the frozen material sublimes should be applied for a suitable period to allow substantial drying of the composition. In one aspect the drying pressure is applied to the frozen composition comprising micro-organisms for a period of from 6 to 120 hours, preferably from 6 to 96 hours, preferably from 12 to 96 hours, preferably for a period of from 24 to 72 hours.

It will be understood by one skilled in the art that the drying pressure as defined in the present invention may be applied during the entire drying process. By way of example only, the entire drying process could be from 5 hours up to several days. In a particular embodiment the drying pressure as defined in the invention is applied until the pellets had an Aw (activity of water) below 0.15.

However in a particular embodiment the drying pressure as defined in the invention is applied during only a part of the drying process, such as for example during the first part, in the middle and/or at the end of the drying process. In a particular embodiment the drying pressure as defined in the invention is applied for example during the first part, in the middle and/or at the end of the primary drying phase. The primary drying phase can be defined as that part of the freeze drying process that involves the sublimation of ice. In contrast, secondary drying involves the desorption of bound water.

In another embodiment, the drying can start using a low standard pressure (e.g. 100 mT) then the drying pressure can be increased to a value as defined in the present invention.

The drying pressure as defined in the invention can therefore be applied during a period of from 5 to 100% of the drying time, preferably from 10 to 100%, preferably from 20 to 100%, preferably from 30 to 100%, preferably from 40 to 100%, preferably from 50 to 100%, preferably from 60 to 100%, preferably from 70 to 100%, preferably from 80 to 100%, preferably from 90 to 100% of the drying time. In a particular example, the drying pressure as defined in the invention is applied during the entire drying process (100% of the drying time). The drying pressure as defined in the invention can therefore be applied during a period of from 5 to 100% of the primary drying phase time, preferably from 10 to 100%, preferably from 20 to 100%, preferably from 30 to 100%, preferably from 40 to 100%, preferably from 50 to 100%, preferably from 60 to 100%, preferably from 70 to 100%, preferably from 80 to 100%, preferably from 90 to 100% of the primary drying phase time. In a particular example, the drying pressure as defined in the invention is applied during the entire primary drying phase (100% of the primary drying time).

The freeze dried composition may be further treated after freeze drying. In one aspect the freeze dried composition is milled after completion of step (i).

Food or Feed

As discussed herein, the present invention further provides a process for the preparation of a food or feed, the process comprising preparing a freeze dried micro-organism composition in accordance with the present process;

combining the freeze dried micro-organism composition with a foodstuff or feedstuff.

a freeze dried micro-organism composition obtainable by a process as defined herein.

a freeze dried micro-organism composition prepared by a process as defined herein.

a food or feed comprising (a) a freeze dried micro-organism composition as defined herein; and (b) a foodstuff or feedstuff.

According to the present invention "food" means products suitable for human consumption. They are materials which contain or consist of essential body nutrients, such as carbohydrates, fats, proteins, vitamins, or minerals, and is ingested and assimilated by an organism to produce energy, stimulate growth, and maintain life, presented in the form of a solid, liquid or paste for consumption. These materials are often combined and mixed at high temperature and contain high humidity. The freeze dried micro-organisms of the present invention are suitable for use in food products. They can be mixed with the food materials which can be subsequently baked, steam treated, compressed, granulated and/or moulded (nutritional bars, string cheese, breakfast cereals, etc).

The freeze dried micro-organisms of the present invention can be used as starter, such as dairy starter. The freeze dried micro-organisms of the present invention can be used as an ingredient in the preparation of foods and they are added to foodstuff. A foodstuff is an ingredient that is suitable for human consumption either alone or when mixed with other ingredients. A particular example of foodstuff is milk of animal and/or plant origin, such as cows milk, that can be fermented by the freeze dried micro-organisms of the present invention to obtain food products.

Foods (or food products) can be selected from the group comprising nutritional bars, breakfast cereals, infant formulas, biscuits cakes, cake mixes, snack foods, balanced foods and drinks, fruit fillings, cake glaze, chocolate bakery fillings, cheese cake flavoured fillings, fruit flavoured cake fillings, cake and doughnut icings, instant bakery filling creams, filings for cookies, ready-to-use bakery fillings, reduced calorie fillings, desserts, confectionery products (e.g. gummi bears, candies, chocolates and chocolate chips, pralines, chewing gums, popcicles), beverages such as beverage powders, soft drinks, fruit juices, beverages comprising whey proteins, health teas, cocoa drinks, milk-based drinks, calcium fortified soy plain and chocolate milks, calcium fortified coffee beverages, lactic acid bacteria-based drinks, adult nutritional beverages, acidified soy/juice beverages, aseptic/retorted chocolate drinks, yoghurts, drinking yoghurts, cheeses, string cheeses, recombined cheeses, ice creams, sherbets, meats.

In a specific embodiment, the food product is a dairy product. Examples of dairy products according to the invention are fermented milk, yoghurt, drinking yoghurt, matured cream, cheese, fromage frais, string cheese, milk-based drink, dairy product retentate, processed cheese, recombined cheese, cream dessert, cottage cheese and infant milk.

Among preferred products are dietary supplements, dairy starters, dairy products and meat products.

According to the present invention "feed" means products suitable for animal consumption and can be selected from the group comprising "pet foods" (cakes, biscuits, chews, snacks . . . for pets), silage products and pelleted feeds. The term "animal" has to be understood under a wide meaning.

It can refer to a "polygastric herbivore" which includes, but is not limited to, bovinae, cervidae, antilocapridae and camelidae. It can refer for example to a "polygastric ruminant" which includes, but is not limited to cows, sheep, ewes, goats, deers, camels, giraffes. It can also refer to a "monogastric herbivore" such as equines and porcines as well as to domesticated animal or pets (e.g. dogs, cats, rabbits, birds, rats, mice, guinea pigs, fish, reptiles . . . ). It can also refer to poultry, chicken, chick and also to any kind of animals from aquaculture area such as shrimps etc.

The freeze dried micro-organisms of the invention may be added to feedstuff (an ingredient that is suitable for animal consumption either alone or when mixed with other ingredients) such as unpelletized feed mixture, which may be subsequently treated with steam and/or which are steam pelleted or dried. The unpelleted mixture refers to premixes and mashes. "Premixes" typically contain vitamin and minerals. Other ingredients such as grains and clays may also be added to premixes. "Mashes" typically contain the complete animal diet. "Pellets" are particles of spherical or cylindrical shape typically created by compressing the original feed mixture which can contain the coated dehydrated micro-organisms of the invention. Before compression, the feed mixture is steamed treated in a conditioner for 30 seconds to 5 min at temperature varying from 60° C. to 95° C. using injected steam.

Freeze-Dried Micro-Organisms Characteristics

In one aspect the present invention provides use of drying pressure to prepare a freeze dried micro-organism composition having improved stability and/or improved cell count and/or increased density and/or improved dispersibility, wherein a drying pressure of from 133 Pa [1000 mT] to 338 Pa [2530 mT] is applied to a frozen composition comprising micro-organisms to dry the frozen composition by sublimation of water present in the frozen composition.

The present invention provides novel drying techniques for the preparation of freeze dried compositions containing micro-organisms. In particular the present invention provides a process in which frozen compositions containing micro-organisms are freeze-dried.

In this process freeze-drying is performed at pressures which are much higher than those normally used for freeze-drying. The skilled man would not have expected to obtain increased micro-organisms characteristics such as stability since he could have thought that a high pressure would have been damageable for the micro-organisms. An advantage of the present invention is that this process (i.e. the use of a high pressure for freeze-drying micro-organisms) may be implemented in different drying techniques such as pellet drying and tray-drying, leading to improved results.

In comparison with the pellets obtained using standard freeze-drying techniques (such process using a pressure of 100 mT), both cell counts, stability, density and dispersibility of the freeze-dried micro-organisms are enhanced.

In comparison with standard tray-drying process, it has been found that the cell counts and the cell stability of the compositions freeze-dried in accordance with the present invention surpass the ones obtained for commercially tray-dried material. Furthermore the bulk density of freeze-dried compositions in accordance with the present invention after milling is equivalent to the best tray-dried products. Moreover scanning electron microscopy (SEM) images indicate that cells of micro-organisms in the present compositions are encapsulated in a matrix; it is understood that this translates to their better stability.

A freeze dried micro-organism composition having improved stability and/or improved cell count and/or increased density and/or improved dispersibility, means that it has one or more of stability (expressed in percent survival) increased of at least 2 fold, preferably at least 3 fold, preferably at least 4 fold, preferably at least 5 fold, preferably at least 6 fold, preferably at least 7 fold, preferably at least 8 fold, preferably at least 9 fold cell count (expressed in cfu or colony forming unit per gram) increased of at least 2 fold, preferably at least 3 fold density (defined as its mass per unit volume) increased at least 2 fold dispersibility increased at least 1.5 fold in comparison with the standard pellet freeze drying process.

The term "stability" should be understood as the viability of a micro-organism over a certain period of time.

The term "dispersibility" should be understood as the ability of a micro-organism composition to disperse/suspend/dissolve/scatter in an aqueous solution.

The present invention will now be described in further detail by way of example only with reference to the accompanying figures in which:

FIG. 1 shows Scanning electron microscope (SEM) images of the interior of a conventionally freeze-dried pellet of a strain of S. thermophilus. (a) 54× magnification of dried pellet; (b) 540× magnification of dried pellet; (c) 2700× magnification of dried pellet. The images demonstrate a finely textured and homogeneous structure of the cell/protectant matrix.

FIG. 2 represent Scanning electron microscope (SEM) images of the interior of a high-pressure freeze-dried pellet of the same strain of S. thermophilus. (a) 34× magnification of dried pellet; (b) 540× magnification of dried pellet; (c) 2700× magnification of dried pellet (what look like holes in this photo are pits where individual cells have been knocked out of place on this fractured surface).

The images demonstrate a rearrangement of the structure of the cell/protectant matrix.

The present invention will now be described in further detail in the following examples.

EXAMPLES

Introduction

Scanning electron microscopy (SEM) image comparisons of conventionally freeze-dried pellets and high-pressure freeze-dried pellets demonstrate real differences in the physical characteristics resulting from the two processes. Cryogenically frozen pellets from a lot of a strain of *Streptococcus thermophilus* were divided into two groups. Half the pellets were dried with a conventional freeze drying cycle using a 100 mTorr vacuum setting, the other half of the pellets were dried with a high-pressure cycle using a 1400 mTorr vacuum setting. FIG. 1 shows that conventionally freeze-dried bacterial pellets have a uniform friable structure consisting of narrow interstitial matrix and open channels, at times each no thicker than a single 1.0 µm bacterium. FIG. 2 shows that the high-pressure freeze-dried bacterial pellets have a less organized matrix, in which the interior of a high-pressure dried pellet has been rearranged. Open spaces have been converted from narrow channels to an interconnected series of spherical voids, and bacteria have become encapsulated in thick bands of matrix.

Scanning electron microscopy was performed on a JEOL JCM 5000 NeoScope SEM. Samples were prepared for SEM imaging by coating with 4-6 nm gold plate using a Cressington 108 sputter coater.

Experimental

*Streptococcus thermophilus* was produced by batch fermentation. Cells were washed by the addition of tap water to the cell fermentate on a 1:1 basis, and cells were concentrated by centrifugation to achieve a cell density of approximately 3.0E+11 cfu/ml to 4.0E+11 cfu/ml. A standard solution of trehalose, a known protectant, was added to the cell concentrate. The cell concentrate/protectant combination was thoroughly mixed, and the mixture was dripped into liquid nitrogen to form frozen pellets. Frozen pellets were stored at −85° C. until the drying experiments were performed.

100 gr aliquots of frozen pellets of *Streptococcus thermophilus* were dried in a Virtis Genesis 35 EL freeze drier at various pressures:

for example 1: 100, 1425 mT and 2010 mT; and
for example 2: 100, 1000 and 1400 mT.

The layer of frozen pellets varied from 1.6 to 3.8 cm. For all the experiments, the shelf temperature was controlled at 25° C. Drying was held until the temperature of the pellets was stable and close to 25° C. The frozen pellets were dried for a period such that at the end of the freeze drying cycle freeze dried pellets were provided having an Aw below 0.15.

Material was then milled using a lab scale mill (Jupiter Family Grain Mill) to provide a powder with a particle size smaller than 30 mesh. The freeze dried pellets and freeze dried powder were then characterized with a series of test. The water content of the dried pellets was assessed by measuring the activity of water (Aw) using an Hygrolab Aw meter (Rotronic). The cell concentration of the dried pellets was measured by resuscitating the cells in a peptone buffer for 2 minutes under agitation then plated using an Ellikers media (DIFCO). Incubation was performed at 38° C. for 48 h. Storage stability of the freeze dried pellets was assessed with an accelerated shelf-life test which consists of placing for 14 days the freeze dried material into an incubator set at 38° C. and measuring the cell counts after that period of time. Then a survival percent was calculated by dividing the cell counts obtained after 14 days by the initial cell counts.

The bulk density of the powder was calculated by measuring the weight of a 10 ml freeze dried powder. The tap density was measured by taping the graduated cylinder until a constant volume was achieved. The tap density was calculated by dividing the weight by the volume obtained after taping. The dispersibility of the freeze dried powder into water was assessed by dropping a spoonful of powder (2 gr) into 100 ml of water at room temperature, then observing if the powder was floating at the surface or sinking quickly after 1minute and 2 minutes. Then the water was mixed for 10 seconds and the solution was observed and the quantity of residual powder floating or decanting at the bottom was visually estimated. A dispersibility index was then calculated with a scale from 1 to 5, with an index of 5 representing a highly dispersable powder (like powder sinking to the bottom in less than 1 minute and no particles floating or at the bottom of the container after mixing) and an index of 1 representing a poorly dispersible powder (no powder sinking within 2 minutes and most particles floating or at the bottom after mixing)

Example 1

A first set of data was collected showing that the bulk and tap density increases as a function of the drying pressure. In addition it can be noted that the cell counts for a drying pressure of 1425 and 2010 mT was higher than when drying pressure was set at 100 mT.

| Drying pressure (mTorr) | Aw | CFU/gr | Bulk density (g/ml) | Tap density (g/ml) |
| --- | --- | --- | --- | --- |
| 100 | 0.004 | 5.10E+11 | 0.20 | 0.33 |
| 1425 | 0.092 | 8.54E+11 | 0.44 | 0.58 |
| 2010 | 0.02 | 7.80E+11 | 0.58 | 0.74 |

Example 2

In the second series of experiment, stability and dispersibility were evaluated. The testing of culture dried by tray was also tested in parallel (the material dried by tray was done in an industrial setting). The data show that not only the drying at a pressure in accordance with the present invention increased the density of the powder, but also improved the dispersibility, cell counts and stability when compared to the powder coming from a pellet drying process at 100 mT. The density and dispersibility are of powder dried in accordance with the present invention also approached the density and dispersibility of the powder with the tray process.

In this experiment we obtained freeze dried micro-organism composition having an improved stability, an improved cell count, an increased density and an improved dispersibility. Indeed:

stability was increased of at least 9 fold in comparison with the standard pellet freeze drying process;
cell count was increased of at least 3 fold in comparison with the standard pellet freeze drying process;
density was increased at least 2 fold in comparison with the standard pellet freeze drying process;
and dispersibility was increased at least 1.5 fold in comparison with the standard pellet freeze drying process.

| Drying process | Drying pressure (mTorr) | Shelf temperature (deg ° C.) | Aw | Cell count | Percent cell survival after 14 days at 38° C. | Bulk density | Tap density | Dispersibility |
| --- | --- | --- | --- | --- | --- | --- | --- | --- |
| Pellets | 100 | 25 | 0.008 | 2.6E11 | 8 | 0.25 | 0.31 | 1.5 |
| Pellets | 1000 | 25 | 0.071 | 7E11 | 65 | 0.50 | 0.64 | 2.3 |
| Pellets | 1400 | 25 | 0.075 | 6.5E11 | 63 | 0.47 | 0.57 | 2.1 |
| Tray | 100 | Variable | 0.046 | 5.5E11 | 37.5 | 0.57 | 0.71 | 3.5 |

Example 3

*Lactobacillus acidophilus* was produced by batch fermentation and concentrated by centrifugation. Then trehalose and phosphate were mixed with the concentrated culture in standard amounts to lyoprotect the strain, and the mixture was dripped into liquid nitrogen to form frozen pellets. Frozen pellets were stored at −85° C. until the drying experiments were performed.

100 gr aliquots of frozen pellets of *Lactobacillus acidophilus* were dried in a Virtis Genesis 35 EL freeze drier at various pressures: 100 mT, 450 mT, 700 mT, 1000 mT and 1250 mT with a shelf temperature of 15° C. The layer of frozen pellets was approximately 2 cm. Drying was held until the temperature of the pellets was stable and close to 15° C. Aw's of freeze dried material are reported in the following Table.

| Drying pressure (mTorr) | Aw |
|---|---|
| 100 | 0.07 |
| 450 | 0.124 |
| 700 | 0.136 |
| 1000 | 0.181 |
| 1250 | 0.21 |

In conclusion, this example shows that a strain protected with a phosphate based protectant has an Aw rising as a function of the applied pressure.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology, food science or related fields are intended to be within the scope of the following claims.

The invention claimed is:

1. A process for the preparation of freeze dried micro-organism composition, comprising the step of:
   (i) subjecting a frozen composition comprising micro-organisms to a drying pressure of from 133 Pa [1000 mT] to 200 Pa [1500 mT] such that at the drying pressure the frozen composition is dried by sublimation of water present in the frozen composition to provide a freeze dried composition comprising the micro-organisms, wherein the micro-organisms are subjected to drying during a primary and a secondary drying phase and wherein the drying pressure is applied to the micro-organisms through the entire primary drying phase.

2. A process according to claim 1 wherein the micro-organisms are selected from the group consisting of yeasts, moulds, fungi, bacteria and mixtures thereof.

3. A process according to claim 1 wherein the micro-organisms are selected from one or more strains of bacteria.

4. A process according to claim 3 wherein the one or more strains of bacteria are selected from lactic acid bacteria.

5. A process according to claim 4 wherein the lactic acid bacteria are selected from *Streptococcus thermophilus* and *Lactobacillus acidophilus*.

6. A process according to claim 1 wherein the frozen composition is in the form of frozen pellets.

7. A process according to claim 1 wherein the process comprises the additional step of (i') freezing a composition comprising micro-organisms to provide the frozen composition of step (i).

8. A process according to claim 1 wherein the freeze dried micro-organism composition comprises the one or more strains of bacteria in an amount of 1E8 to 5E12 CFU/g of freeze dried micro-organism composition.

9. A process according to claim 1 wherein in step (i) the composition is subjected to a temperature of from 10 to 40° C.

10. A process according to claim 1 wherein in step (i) the composition is subjected to a temperature of approximately 25° C.

11. A process according to claim 1 wherein the drying pressure is applied to the frozen composition comprising micro-organisms for a period of from 24 to 72 hours.

12. A process according to claim 1 wherein the freeze dried composition is subsequently milled.

13. A process for the preparation of a food or feed, the process comprising
   (a) preparing a freeze dried micro-organism composition in accordance with claim 1; and
   (b) combining the freeze dried micro-organism composition with a foodstuff or feedstuff.

14. A freeze dried micro-organism composition prepared by a process as defined in claim 1.

15. A food or feed comprising
   (a) a freeze dried micro-organism composition as defined in claim 14; and
   (b) a foodstuff or feedstuff.

16. A method of preparing a freeze dried micro-organism composition having improved stability and/or improved cell count and/or increased density and/or improved dispersibility, the method comprising:
   applying a drying pressure of from 133 Pa [1000 mT] to 200 Pa [1500 mT] to a frozen composition comprising micro-organisms to dry the frozen composition by sublimation of water present in the frozen composition, wherein the micro-organisms are subjected to drying during a primary and a secondary drying phase and wherein the drying pressure is applied to the micro-organisms through the entire primary drying phase.

* * * * *